United States Patent [19]

Schmitt et al.

[11] Patent Number: 4,457,930
[45] Date of Patent: Jul. 3, 1984

[54] TODOPROPARGYLSULPHAMIDES, MICROBICIDAL COMPOSITIONS AND USE

[75] Inventors: Hans-Georg Schmitt, Leverkusen; Wilfried Paulus; Hermann Genth, both of Krefeld; Wilhelm Brandes, Leichlingen; Paul Reinecke; Hans Scheinpflug, both of Leverkusen, all of Fed. Rep. of Germany

[73] Assignee: Bayer Aktiengesellschaft, Leverkusen, Fed. Rep. of Germany

[21] Appl. No.: 526,930

[22] Filed: Aug. 26, 1983

[30] Foreign Application Priority Data

Sep. 14, 1982 [DE] Fed. Rep. of Germany ....... 3234037

[51] Int. Cl.$^3$ ..................... A01N 41/02; A01N 43/84; C07D 295/22; C07C 161/00
[52] U.S. Cl. .................. 424/248.5; 424/246; 424/250; 424/267; 424/274; 424/283; 424/285; 424/304; 424/310; 424/324; 424/320; 71/88; 71/92; 71/94; 71/95; 71/103; 544/58.1; 544/58.2; 544/159; 544/383; 546/232; 546/246; 548/542; 549/426; 549/495; 560/13; 564/79; 260/465 E; 106/18.33; 524/168; 524/169
[58] Field of Search ...................... 544/159, 383, 58.1, 544/58.2; 546/232, 246; 548/542; 549/426, 495; 564/79; 560/13; 260/465 E; 424/246, 248.5, 250, 267, 274, 283, 285, 304, 310, 324, 320; 71/88, 92, 94, 95, 103; 106/18.33

[56] References Cited

U.S. PATENT DOCUMENTS 3,351,584 11/1967 Houlihan .............................. 564/79

OTHER PUBLICATIONS

Kobayashi et al., *Chemical Abstracts*, vol. 89, (1975), No. 155408f.

*Primary Examiner*—Robert W. Ramsuer
*Attorney, Agent, or Firm*—Sprung, Horn, Kramer & Woods

[57] ABSTRACT

3-Iodopropargyl-sulphamides of the formula

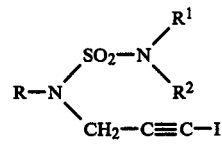

in which
R represents hydrogen, alkyl, optionally substituted cycloalkyl, optionally substituted phenylalkyl, optionally substituted heterocyclylalkyl or optionally substituted phenyl, and
$R^1$ and $R^2$ are identical or different and represent alkyl, or
$R^1$ and $R^2$ represent an alkylene bridge which, together with the nitrogen atom at which they are located, form a ring which can be interrupted by further hetero atoms,
which are microbicidally active.

15 Claims, No Drawings

TODOPROPARGYLSULPHAMIDES, MICROBICIDAL COMPOSITIONS AND USE

The present invention relates to new iodopropargylsulphamides, a process for their preparation and their use as pest-combating agents.

It has already been disclosed that a number of organic compounds, such as, for example, zinc ethylene-1,2-bis-(dithiocarbamate) or N-trichloromethylthio-tetrahydrophthalimide, possess fungicidal and bactericidal properties (see, for example, R. Wegler, "Chemie der Pflansenschutz- und Schädlingsbekämpfungsmittel" [Chemistry of Plant Protection Agents and Pest-Combating Agents], Springer Verlag Chemie, Volume 2). However, the action is not always completely satisfactory, particularly when low amounts and concentrations are used.

N-iodopropargylsulphamides having microbicidal activity have also been described (see Japanese Application 74,100,037). Furthermore, dichlorofluoromethanesulphenylsulphamides are known, which possess fungicidal activity and are used in plant protection, and in addition can be used in microbicidal agents for the protection of industrial materials (see "Angewandte Chemie", 76, 807 (1964), and Dutch patent specification No. 6,504,561).

New iodopropargylsulphamides of the general formula (I)

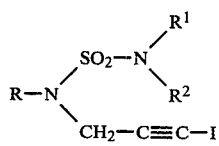
(I)

in which
  R represents hydrogen, alkyl, optionally substituted cycloalkyl, optionally substituted phenylalkyl, optionally substituted heterocyclylalkyl or optionally substituted phenyl,
  $R^1$ and $R^2$ are identical or different and represent alkyl, or
  $R^1$ and $R^2$ represent an alkylene bridge which, together with the nitrogen atom at which they are located, form a ring which can be interrupted by further hetero atoms.

Furthermore, it has been found that the new iodopropargylsulphamides of the formula (I)

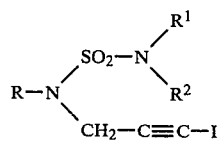
(I)

in which
  R represents hydrogen, alkyl, optionally substituted cycloalkyl, optionally substituted phenylalkyl, optionally substituted heterocyclylalkyl or optionally substituted phenyl,
  $R^1$ and $R^2$ are identical or different and represent alkyl, or
  $R^1$ and $R^2$ represent an alkylene bridge which, together with the nitrogen atom at which they are located, form a ring which can be interrupted by further hetero atoms,
are obtained when propargylsulphamides of the formula (II)

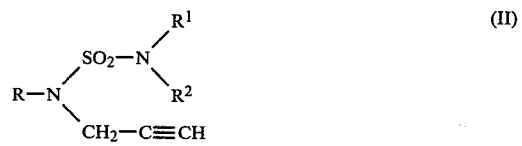
(II)

in which
  R, $R^1$ and $R^2$ have the meaning given above,
are reacted with iodine in the presence of a base and, if appropriate, in the presence of a solvent or diluent.

The new iodopropargylsulphamides of the formula (I) possess microbicidal properties. In this respect, the compounds according to the invention, of the formula (I), surprisingly exhibit better microbicidal activity than the fungicidal and bactericidal substances known from the prior art, such as, inter alia, zinc ethylene-1,2-bis-(dithiocarbamate) and N-trichloromethylthio-tetrahydrophthalimide. The substances according to the invention thus represent an enrichment of the art.

Formula (I) gives a general definition of the iodopropargylsulphamides according to the invention. In this formula,
  R preferably represents hydrogen, straight-chain or branched alkyl having 1 to 18 carbon atoms or cycloalkyl which has 3 to 8 ring members and is optionally monosubstituted to pentasubstituted by alkyl having 1 to 6 carbon atoms, or represents phenylalkyl which has 1 to 4 carbon atoms in the alkyl part and is optionally monosubstituted to pentasubstituted in the phenyl ring by alkyl having 1 to 4 carbon atoms and/or halogen, or represents heterocyclylalkyl which has 1 to 4 carbon atoms in the alkyl part and 5 to 8 ring members in the heterocyclyl part and is optionally monosubstituted to tetrasubstituted by identical or different substituents from amongst alkyl having 1 to 4 carbon atoms and/or halogen, it being possible for the heterocyclyl part to contain 1 to 3 hetero atoms, such as nitrogen, oxygen and/or sulphur, or represents phenyl which can be monosubstituted to pentasubstituted by identical or different substituents from amongst halogen, cyano, nitro, alkyl having 1 to 5 carbon atoms, alkoxy having 1 to 5 carbon atoms, alkylthio having 1 to 5 carbon atoms, alkoxycarbonyl having 1 to 5 carbon atoms in the alkoxy part, halogenoalkyl or halogenoalkoxy or halogenoalkylthio or halogenoalkylsulphonyl having 1 to 5 carbon atoms and 1 to 5 halogen atoms in each halogenoalkyl radical,
  $R^1$ and $R^2$ preferably represent identical or different alkyl radicals, each having 1 to 5 carbon atoms, or
  $R^1$ and $R^2$ represent an alkylene bridge having 2 to 8 carbon atoms, which, together with the nitrogen at which they are located, form a ring which can be interrupted by further hetero atoms, such as oxygen, sulphur or the groups SO or $SO_2$, or by N-alkyl. The rings can be optionally monosubstituted to pentasubstituted by alkyl having 1 to 6 carbon atoms.

Particularly preferred compounds of the formula (I) are those in which

R represents hydrogen, straight-chain or branched alkyl having 1 to 12 carbon atoms, or cycloalkyl which has 3 to 6 ring members and is optionally monosubstituted to trisubstituted by alkyl having 1 to 4 carbon atoms, or represents phenylalkyl which has 1 or 2 carbon atoms in the alkyl part and is optionally monosubstituted to pentasubstituted in the phenyl ring by identical or different substituents from amongst alkyl having 1 to 3 carbon atoms and/or fluorine, chlorine, bromine or iodine, or represents heterocyclylalkyl which has 1 or 2 carbon atoms in the alkyl part and 5 or 6 ring members in the heterocyclyl part and is optionally monosubstituted to trisubstituted by identical or different substituents from amongst methyl, ethyl, fluorine, chlorine, bromine, it being possible for the heterocyclyl part to contain 1 or 2 identical or different hetero atoms, such as nitrogen or oxygen, or represents phenyl which can be monosubstituted to trisubstituted by identical or different substituents from amongst fluorine, chlorine, bromine, cyano, nitro, alkyl having 1 to 3 carbon atoms, such as methyl, ethyl, n-propyl or isopropyl, methoxy, ethoxy, trifluoromethyl, trifluoromethoxy, trifluoromethylthio, difluorochloromethyl, difluorochloromethoxy, difluorochloromethylthio, trifluoromethylsulphonyl, methoxycarbonyl or ethoxycarbonyl, and $R^1$ and $R^2$ are identical or different and represent alkyl having 1 to 3 carbon atoms, or $R^1$ and $R^2$ represent an alkylene bridge having 2 to 5 carbon atoms, which, together with the nitrogen atom at which they are located, form a ring which can be interrupted by further hetero atoms, such as oxygen, sulphur or N-alkyl having 1 to 3 carbon atoms.

If N-(3-fluorophenyl)-N-propargyl-N'-ethyl-N'-n-propylsulphamide and iodine are used as starting materials in the presence of a base, the course of the reaction of the process according to the invention, for the preparation of the new compounds, can be represented by the following equation:

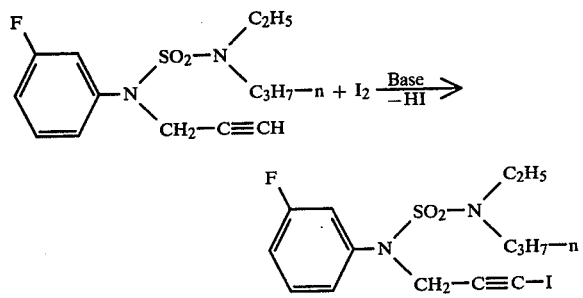

Formula (II) gives a general definition of the propargylsulphamides to be used as starting materials in carrying out the process according to the invention. Some of these compounds are known (see Dutch Patent Application No. 6,500,481). The new starting compounds can also be prepared by known processes, for example if (a) a sulphamide of the formula (III)

in which
Y represents hydrogen or one equivalent of an alkali metal, such as lithium, potassium or sodium, and
R, $R^1$ and $R^2$ have the meaning given above,
is reacted with a propargyl halide of the formula (IV)

in which
Hal represents halogen, such as chlorine, bromine or iodine,
if appropriate in the presence of a base, or (b) a propargylamine of the formula (V)

in which
R has the meaning given above,
is reacted with a sulphamoyl chloride of the formula (VI)

in which
$R^1$ and $R^2$ have the meaning given above.

Iodine, which is additionally to be used as a starting material, is a commercially available substance.

The process according to the invention, for the preparation of the new compounds of the formula (I), is carried out in the presence of a base. All customarily usable bases can be employed. These include, for example, alkali metal hydroxides, such as sodium hydroxide or potassium hydroxide, as well as tertiary amines.

Preferred solvents or diluents for the process according to the invention are all inert solvents. These include ethers, such as dioxane, tetrahydrofuran or glycol dimethyl ether. Furthermore, alcohols, such as methanol or ethanol, can be used, and the reaction can also be carried out in water or, preferably, in mixtures of solvents and water.

In carrying out the process according to the invention, the reaction temperature can be varied within a relatively wide range. In general, the reaction is carried out at between −10° C. and 40° C., preferably between 0° C. and 20° C.

The process according to the invention is carried out in general under atmospheric pressure.

To carry out the process according to the invention, between 1 and 1.5 mols, preferably between 1.0 and 1.3 mols, of iodine are usually employed per mol of propargylsulphamide of the formula (II).

To carry out the process according to the invention, between 1 and 10 mols, preferably between 1 and 5 mols, of a base are usually employed per mol of propargylsulphamide of the formula (II).

The reaction is preferably carried out as follows: a propargylsulphamide of the formula (II), in one of the solvents stated above or a mixture thereof with water, is initially introduced, and one of the bases stated above is added dropwise, while maintaining the stated temperature. Thereafter, the iodine is added, and the reaction mixture is stirred further for some time at the required temperature. The working-up of the reaction mixture and the isolation of the reaction product according to the invention, of the formula (I), are effected in a generally customary manner.

Some of the compounds according to the invention are solids, and some of them are oils which are difficult to crystallise.

To prepare the starting materials of the formula (II), sulphamides (see Dutch Pat. No. 6,414,819) are reacted with propargyl halides in the presence of a base, as described above. Particularly suitable bases are tertiary amines, such as triethylamine and dimethylaniline, or carbonates, for example potassium carbonate or sodium carbonate, and suitable solvents are: alcohols, for example ethanol, propanol and butanol, or ethers, for example dioxane and tetrahydrofuran, or hydrocarbons, for example toluene, chlorohydrocarbons, such as chloroform, or amides, such as dimethylformamide.

In a preferred embodiment, the reaction of the sulphamides of the formula (III) with a propargyl halide is carried out in the presence of sodium hydroxide or potassium hydroxide as the base, and of a phase-transfer catalyst, such as tetrabutylammonium bromide, triethylbenzylammonium chloride or methyltrioctylammonium chloride. Water is used as the diluent.

In a particularly preferred embodiment, alkali metal salts of the sulphamides of the general formula (III) are reacted with a propargyl halide.

Preferred alkali metal salts are the sodium salt and the potassium salt. The salts can be prepared by adding an appropriate base, for example in the form of an aqueous, alcoholic or ethereal dilution of the parent compounds.

Preferred propargyl halides are 3-chloroprop-1-yne and 3-bromoprop-1-yne.

Alcohols, such as methanol and ethanol, ethers, such as dioxane and glycol dimethyl ether, or amides, such as dimethylformamide, are used as diluents.

The reaction temperatures can be varied over a relatively wide range, and the reaction is carried out in general at between 20° C. and 100° C., preferably at 40° C.–80° C.

In carrying out the process for the preparation of the starting compounds, the components are employed in general in equimolar amounts, but is is sometimes advantageous to employ the propargyl halide in an excess of up to 50% in order to complete the reaction.

The working-up can be carried out, for example, as follows:

After the reaction is complete, the diluent is removed by distillation, the residue is taken up in a halohydrocarbon, such as chloroform or methylene chloride, the organic phase is washed with water, and the solvent is then evaporated down.

Some of the propargylsulphamides are solids, and some of them are oils which can be purified by distillation under reduced pressure and at temperatures below 100° C.

Propargylamines of the formula (V) which are required for the preparation of the starting materials of the formula (II) are generally known and can be prepared by processes known from the literature (see, for example, Liebigs Annalen Chem. 576, 35, (1952)). In process b) for the preparation of the starting compounds of the formula (II), the reaction is also advantageously carried out in the presence of a base, in particular tertiary amines, such as triethylamine or dimethylaniline, being suitable.

Inert solvents can be employed as diluents. These include ethers, such as tetrahydrofuran and dioxane, hydrocarbons, such as toluene, and amides, such as dimethylformamide and dimethylacetamide.

In general, the reaction is carried out at 20°–100° C., preferably at 40°–80° C.

The reactants are customarily employed in a molar ratio.

Owing to the powerful microbicidal action, the active compounds according to the invention can be employed in practice for combating undesired microorganisms. The active compounds are suitable for use as plant protection agents and as fungicidal agents for the protection of industrial materials.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention, of the formula (I), can be used with particularly good success inter alia for combating rice diseases, such as, for example, *Pyricularia oryzae*, and in addition for combating the apple scab causative organism, such as, for example, *Venturia inaequalis*, and furthermore against *Phytophthora infestans* and *Puccinia recondita*.

When used appropriately and in appropriate concentration, the compounds also exhibit bactericidal activity.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalene, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

When used in plant protection, the active compounds according to the invention can be present in the formulations or in the various forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsion, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

The iodopropargylsulphamides according to the invention, of the formula (I), are also suitable as microbicidal agents for the protection of industrial materials.

Incorporating the active compounds according to the invention into industrial materials which are exposed to attack by fungi and bacteria inhibits the growth of the fungi and bacteria; hence, the original value of the materials is preserved.

Industrial materials within the scope of the present invention are products which themselves do not occur in nature but are manufactured from natural or synthetic starting materials. The products within the scope of the present invention which are to be protected are industrial materials which can be decomposed by micro-organisms.

Examples of industrial materials which are to be protected by the substances according to the invention from microbial modification and destruction are adhesives, glues, papers and cardboards, textiles, leather, wood, paints, plasters, cooling lubricants and plastic articles, which can be attacked and destroyed by micro-organisms. Parts of production plants, such as, for example, cooling water circulations and cooling lubricant circulations, the efficiency of which can be adversely affected by microorganisms, may also be mentioned within the scope of the materials to be protected. Preferably, the active compounds according to the invention can be used for the protection of adhesives, paper, cardboard, coatings, wood and the like.

Micro-organisms which can cause degradation or modification of industrial materials are, for example, bacteria, fungi, yeasts, algae and slime organisms. The substances according to the invention are preferentially active against fungi and slime organisms; the fungicidal action is effective against mold as well as wood-destroying and wood-discolouring fungi.

Micro-organisms of the following genera may be mentioned as examples:
Alternaria, such as *Alternaria tenuis*,
Alternaria, such as *Alternaria speciales*,
Aspergillus, such as *Aspergillus niger*,
Chaetomium, such as *Chaetomium globosum*,
Coniophora, such as *Coniophora cerebella*,
Lentinus, such as *Lentinus tigrinus*,
Penicillium, such as *Penicillium glaucum*,
Penicillium, such as *Penicillium citrinum*,
Polyporus, such as *Polyporus versicolor*,
Aureobasidium, such as *Aureobasidium pullulans*,
Schlerophoma, such as *Sclerophoma pityophila*,
Stachybotrys, such as *Stachybotrys atra*,
Paecilomyces, such as *Paecilomyces varioti*,
Cladosporium, such as *Cladosporium herbarum*,
Aspergillus, such as *Aspergillus ustus*,
Aspergillus, such as *Aspergillus flavus*.

Depending on their field of use, the substances according to the invention can be converted to the customary formulations, such as solutions, emulsions, suspensions, powders, pastes and granules. These can be prepared in a manner which is in itself known, for example by mixing the active compounds with an extender which consists of a liquid solvent and/or solid carriers, optionally with the use of surface-active agents, such as emulsifiers and/or dispersing agents, and, for example, in the case in which water is used as extender, organic solvents can, if appropriate, be used as auxiliary solvents.

Organic solvents for the active compounds can be, for example, alcohols, such as lower alcohols, preferably ethanol or isopropanol, or benzyl alcohol, ketones, such as acetone or methyl ethyl ketone, liquid hydrocarbons, such as petroleum, fractions, chlorinated hydrocarbons, such as 1,2-dichloroethane.

The microbicidal agents according to the invention contain in general 10 to 100% by weight, preferably 50 to 80% by weight, of the propargylsulphamides as the active compound.

The use concentration of the substances according to the invention depends on the nature and extent of the micro-organisms to be combated, as well as on the composition of the material to be protected. The optimum use amount can be determined by test series. In general, the use concentrations are in the range from 0.001 to 5% by weight, preferably from 0.5 to 1.0% by weight, relative to the material to be protected.

When used in material protection, the new active compounds according to the invention can also be employed as a mixture with other known active compounds, in particular, for broadening the spectrum of action, with bactericides; phenol derivatives, compounds which are split off formaldehyde, and dithiocarbamates, benzimidazolyl carbamates, thioazolylbenzimidazole, isothiazolone derivatives and benzoisothiazolone derivatives, trihalogenomethylthio compounds, tetrachloroisophthalic acid dinitrile, mercaptobenzothiazole and mercaptopyridine may be mentioned as examples.

In contrast to known microbicidal sulphamides, for example N,N-dimethyl-N'-phenyl-N'-fluorodichloromethylthio-sulphamide, the N-iodopropargylsulphamides according to the invention are distinguished by stability in alkaline media, as a result of which their usefulness as microbicides for the protection of industrial materials is substantially extended.

PREPARATION EXAMPLES

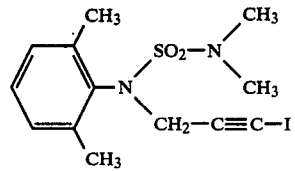

Example 1

(a) 26.6 g (0.1 mol) of N',N'-dimethyl-N-propargyl-2,6-dimethylsulphanilide are dissolved in 200 ml of methanol, and the solution is cooled to −5° C. 75 g of 25% strength sodium hydroxide solution are added dropwise at a rate such that the internal temperature does not exceed 0° C.; thereafter, 34 g of finely powdered iodine are introduced at 0°–5° C., and the mixture is stirred for a further 30 minutes at 0°–5° C. 250 ml of water are allowed to flow in slowly while stirring vigorously, a little 10% strength bisulphite solution is added until the mixture is decolorized and the precipitated product is filtered off under suction. 28 g (71.4% of theory) of N',N'-dimethyl-N-(3-iodopropargyl)-2,6-dimethylsulphanilide are obtained as colorless crystals of melting point 119°–121° C. (from cyclohexane).

The propargylanilide employed as a starting material is prepared in the following manner:

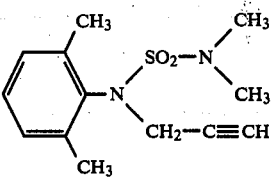

(b) A solution of 17.5 g (0.155 mol) of potassium tert.-butylate in 50 ml of tetrahydrofuran is added to a solution of 34.3 g (0.15 mol) of N',N'-dimethyl-2,6-dimethylsulphanilide in 35 ml of tetrahydrofuran, while cooling. The potassium salt separates out as a viscous mass, which crystallizes through after it has been standing for a short time; it is filtered off under suction, washed with ether and then introduced into a stirred solution of 13 g (0.17 mol) of 3-chloropropyne in 100 ml of dimethylformamide at 0°–5° C. Thereafter, the mixture is warmed slowly to 70° C., and kept at this temperature for 3 hours. The solvent is removed at 70° C. in the vacuum from a water jet, and the residue is poured onto water. The solid which separates out is filtered off under suction, and dried in a desiccator. 36.5 g (91.5% of theory) of N',N'-dimethyl-N-propargyl-2,6-dimethylsulphanilide of melting point 109°–11° C. are obtained (from cyclohexane).

The compounds according to the invention, of the formula (I), can be prepared analogously to the procedure described in Example 1:

| Example No. | R | R¹ | R² | Melting point (°C.); Refractive index [$n_D^{20}$] |
|---|---|---|---|---|
| 2 | ⌬— | CH₃ | CH₃ | 74–75 |
| 3 | CH₃—⌬— | CH₃ | CH₃ | 78–79 |
| 4 | 2-CH₃-⌬— | CH₃ | CH₃ | 75 |
| 5 | 3-CH₃-⌬— | CH₃ | CH₃ | 1.5700 |
| 6 | 2-Cl-⌬— | CH₃ | CH₃ | 82–85 |
| 7 | 3-Cl-⌬— | CH₃ | CH₃ | 55–57 |

| Example No. | R | R¹ | R² | Melting point (°C.); Refractive index [$n_D^{20}$] |
|---|---|---|---|---|
| 8 | Cl—C₆H₄— | CH₃ | CH₂ | 84–85 |
| 9 | 2,3-Cl₂—C₆H₃— | CH₃ | CH₃ | 1.5814 |
| 10 | CF₃O—C₆H₄— | CH₃ | CH₃ | viscous oil |
| 11 | F—C₆H₄— | CH₃ | CH₃ | 67 |
| 12 | CF₃—C₆H₄— | CH₃ | CH₃ | 1.5405 |
| 13 | CF₃S—C₆H₄— | CH₃ | CH₃ | 1.5000 |
| 14 | CH₃ | CH₃ | CH₃ | 36 |
| 15 | C₂H₅ | CH₃ | CH₃ | 48 |
| 16 | i-C₃H₇ | CH₃ | CH₃ | 85.5 |
| 17 | t-C₄H₉ | CH₃ | CH₃ | 65–8 |
| 18 | n-C₁₂H₂₅ | CH₃ | CH₃ | 27 |
| 19 | cyclohexyl | CH₃ | CH₃ | 75–7 |
| 20 | 3,3,5-trimethylcyclohexyl | CH₃ | CH₃ | 85–8 |
| 21 | C₆H₅—CH₂— | CH₃ | CH₃ | 30 |
| 22 | furyl—CH₂— | CH₃ | CH₃ | 1.5411 |
| 23 | H |  | —(CH₂)₂—O—(CH₂)₂— | 74–6 |
| 24 | C₆H₅— |  | —(CH₂)₂—O—(CH₂)₂— | 1.5665 |
| 25 | C₆H₅—CH₂ |  | —(CH₂)₂—O—(CH₂)₂— | 120–21 |
| 26 | Cl—C₆H₄— |  | —(CH₂)₂—O—(CH₂)₂— | 60–2 |
| 27 | cyclohexyl— |  | —(CH₂)₂—O—(CH₂)₂— | 120–2 |
| 28 | CH₃ |  | —(CH₂)₂—O—(CH₂)₂— | 64–6 |
| 29 | C₆H₅— |  | —(CH₂)₅— | 60–2 |
| 30 | C₆H₅—CH₂— |  | —(CH₂)₅— | 65–8 |
| 31 | Cl—C₆H₄— |  | —(CH₂)₅— | 1.5728 |
| 32 | CH₃ |  | —(CH₂)₄— | 82–5 |
| 33 | C₆H₅— |  | —(CH₂)₄— | 75–7 |
| 34 | C₆H₅—CH₂— |  | —(CH₂)₄— | 108–10 |
| 35 | Cl—C₆H₄— |  | —(CH₂)₄— | 92–3 |
| 36 | 2,3-Cl₂—C₆H₃— | CH₃ | CH₃ | 1.5778 |

USE EXAMPLES

The known compounds indicated here are employed as comparative substances in the examples which follow:

(A) N—trichloromethylthio-tetrahydrophthalimide

(B) zinc ethylene-1,2-bis-(dithiocarbamate)

(C) N,N—dimethyl-N'—phenyl-N'—fluorodichloromethyl-thiosulphamide

Example A

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia*

*inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with compound (A) from the prior art is shown, for example, by the compounds according to the following preparation examples: 3, 5, 1, 8, 9, 33, 35, 4 and 6.

Example B

Phytophthora test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabinet at 100% relative atmospheric humidity and at about 20° C.

Evaluation is carried out 3 days after the inoculation.

In this test, a clearly superior activity compared with the prior art is shown, for example, by the compounds according to the following preparation examples: 5, 8, 29, 4 and 6.

Example C

Puccinia test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: 2, 3, 11, 10, 12, 13, 19, 28, 32, 31 and 4.

Example D

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried off, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 3, 29 and 30.

Example E

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 26, 28 and 11.

Example F

Action against fungi

The compounds according to the invention are incorporated, in stepwise concentrations between 0.1 and 5,000 mg/l of test sample, into an agar prepared from beer-wort and peptone. After the agar has solidified, the agar samples thus prepared are contaminated with pure cultures of various test organisms.

After storage for 2 weeks at 28° C. and 60 to 70% relative atmospheric humidity, the evaluation is carried out. The minimum inhibitory concentration (MIC), that is to say the lowest concentration of the substance, present in an agar sample, at which no growth of the species used takes place, is determined.

In this test, a very good action is shown by the compounds according to the following preparation examples: 2, 6, 8, 5, 14, 15, 16, 17, 19 and 22.

Example G

Action against slime organisms

Compounds according to the invention, in concentrations of, in each case, 0.1 to 100 mg/l in Allens nutrient solution (Arch. Mikrobiol. 17, 34 to 53 (1952)) which contains, in 4 liters of sterile water, 0.2 g of ammonium chloride, 4.0 g of sodium nitrate, 1.0 of dipotassium hydrogen phosphate, 0.2 g of calcium chloride, 2.05 g of magnesium sulphate, 0.02 g of iron chloride and 1% of caprolactam, are used in solution in a small amount of acetone. Shortly beforehand, the nutrient solution is infected with slime organisms (approx. $10^6$ germ/ml) which has been isolated from spinning water circulations used in polyamide production. Nutrient solutions which have the minimum inhibitory concentrations (MIC) or higher active compound concentrations are still completely clear after culture for 3 weeks at room temperature, that is to say the pronounced multiplication of microbes and formation of slime which are noticeable after 3 to 4 days in nutrient solutions which are free of active compound, do not occur.

In this test, the compounds according to the following preparation examples were employed: 2, 6, 8, 5, 14, 15 and 22.

Example H

Testing of coatings in respect of resistance to mold

The test is carried out on the basis of Report 219 of the Defense Standards Laboratories, Maibyrnong, Australia, as follows: the product to be tested is applied by means of a brush onto both sides of smooth cardboard, and the coating is dried for 8 days at room temperature. For ageing, a part of the coating is exposed to flowing water at 24° C. for 24 hours, or exposed to fresh air at 40° to 60° C. for 8 days, or subjected to a dry Xenon test for 110 hours. 5×5 cm sections of the samples thus prepared are placed individually in Petri dishes, on a glucose nutrient medium, and are contaminated with a spore suspension of the following fungi: *Aspergillus niger, Pullularia pullulans, Alternaria speciales, Penicillium citrinum, Stachybotrys atra, Paecilomyces varioti, Cladosporium herbarum, Aspergillus ustus* and *Aspergillus flavus.*

The contaminated dishes are stored at 28° to 30° C. and 90 to 95% relative atmospheric humidity, and are evaluated after three weeks. Coatings are considered to be mold-resistant if the samples remain free of fungi after these tests.

Using the test method indicated above, a commercially available, alkaline dispersion paint based on polyvinyl acetate is tested in respect of resistance to mold.

Samples of the paint which contain 1.5-2% (or more), relative to the total solids content, of N,N-dimethyl-N'-phenyl-N'-iodopropargylsulphamide (2) give very good mold-resistant coatings, even when the coatings have been subjected beforehand to the above-mentioned conditions.

It will be appreciated that the instant specification and examples are set forth by way of illustration and not limitation and that various modifications and changes may be made without departing from the spirit and scope of the present invention.

We claim:
1. A 3-iodopropargyl-sulphamide of the formula

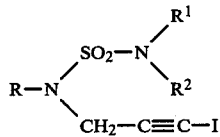

in which
R represents hydrogen, alkyl, optionally substituted cycloalkyl, optionally substituted phenylalkyl, optionally substituted heterocyclylalkyl or optionally substituted phenyl, and
$R^1$ and $R^2$ are identical or different and represent alkyl, or
$R^1$ and $R^2$ represent an alkylene bridge which, together with the nitrogen atom at which they are located, form a ring which can be interrupted by further hetero atoms.

2. A compound according to claim 1, in which
R represents hydrogen, straight-chain or branched alkyl having 1 to 18 carbon atoms or cycloalkyl which has 3 to 8 ring members and is optionally monosubstituted to pentasubstituted by alkyl having 1 to 6 carbon atoms, or represents phenylalkyl which has 1 to 4 carbon atoms in the alkyl part and is optionally monosubstituted to pentasubstituted in the phenyl ring by alkyl having 1 to 4 carbon atoms and/or halogen, or represents heterocyclyalkyl which has 1 to 4 carbon atoms in the alkyl part and 5 to 8 ring members in the heterocyclyl part and is optionally monosubstituted to tetrasubstituted by identical or different substituents from amongst alkyl having 1 to 4 carbon atoms and/or halogen, it being possible for the heterocyclyl part to contain 1 to 3 hetero atoms, or represents phenyl which can be monosubstituted to pentasubstituted by identical or different substituents from amongst halogen, cyano, nitro, alkyl having 1 to 5 carbon atoms, alkoxy having 1 to 5 carbon atoms, alkylthio having 1 to 5 carbon aoms, alkoxycarbonyl having 1 to 5 carbon atoms in the alkoxy part, halogenoalkyl or halogenoalkoxy or halogenoalkylthio or halogenoalkylsulphonyl having 1 to 5 carbon atoms and 1 to 5 halogen atoms in each halogenoalkyl radical, and
$R^1$ and $R^2$ represent identical or different alkyl radicals, each having 1 to 5 carbon atoms, or
$R^1$ and $R^2$ represent an alkylene bridge having 2 to 8 carbon atoms, which, together with the nitrogen at which they are located, form a ring which can be interrupted by further hetero atoms, such as oxygen, sulphur or the groups SO or $SO_2$, or by N-alkyl having 1 to 3 carbon atoms in the alkyl part. And the rings can be optionally monosubstituted to pentasubstituted by alkyl having 1 to 6 carbon atoms.

3. A compound according to claim 1, in which
R represents hydrogen, straight-chain or branched alkyl having 1 to 12 carbon atoms, or cycloalkyl which has 3 to 6 ring members and is optionally monosubstituted to trisubstituted by alkyl having 1 to 4 carbon atoms, or represents phenylalkyl which has 1 or 2 carbon atoms in the alkyl part and is optionally monosubstituted to pentasubstituted in the phenyl ring by identical or different substituents from amongst alkyl having 1 to 3 carbon atoms and/or fluorine, chlorine, bromine or iodine, or represents heterocyclylalkyl which has 1 to 2 carbon atoms in the alkyl part and 5 or 6 ring members in the heterocyclyl part and is optionally monosubstituted to trisubstituted by identical or different substituents from amongst methyl, ethyl, fluorine, chlorine, bromine, it being possible for the heterocyclyl part to contain 1 or 2 identical or different hetero atoms, or represent phenyl which can be monosubstituted to trisubstituted by identical or different substituents from amongst fluorine, chlorine, bromine, cyano, nitro, alkyl having 1 to 3 carbon atoms, methoxy, ethoxy, trifluoromethyl, trifluoromethoxy, trifluoromethylthio, difluorochloromethyl, difluorochloromethoxy, difluorochloromethylthio, trifluoromethylsulphonyl, methoxycarbonyl or ethoxycarbonyl, and $R^1$ and $R^2$ are identical or different and represent alkyl having 1 to 3 carbon atoms, or $R^1$ and $R^2$ represent an alkylene bridge having 2 to 5 carbon atoms, which, together with the nitrogen atom at which they are located, form a ring which can be interrupted by oxygen atoms, sulphur or the N-alkyl group containing 1 to 3 carbon atoms.

4. A compound according to claim 1, in which

R represents hydrogen, alkyl having 1 to 12 carbon atoms, or cyclohexyl or cyclopentyl which is optionally monosubstituted to trisubstituted by methyl, or represents benzyl or furyl, or phenyl which is optionally monosubstituted or disubstituted by identical or different substituents from amongst methyl, chlorine, fluorine, trifluoromethoxy, trifluoromethyl and trifluoromethylthio, and $R^1$ and $R^2$ represent methyl, or $R^1$ and $R^2$ represent an alkylene bridge having 4 or 5 carbon atoms, which, together with the nitrogen atom at which they are located, form a ring which can be optionally interrupted by oxygen.

5. A compound according to claim 1, wherein such compound is N',N'-dimethyl-N-(3-iodopropargyl)-4-methylsulphanilide of the formula

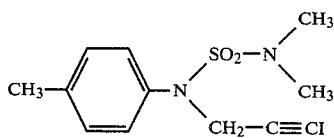

6. A compound according to claim 1, wherein such compound is N',N'-dimethyl-N-(3-iodopropargyl)-4-trifluoromethoxysulphanilide of the formula

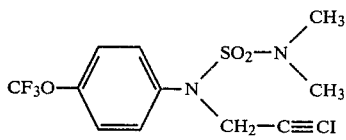

7. A compound according to claim 1, wherein such compound is N',N'-dimethyl-N-(3-iodopropargyl)-4-fluorosulphanilide of the formula

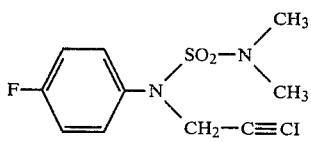

8. A compound according to claim 1, wherein such compound is N',N'-dimethyl-N-(3-iodopropargyl)-4-trifluoromethylsulphanilide of the formula

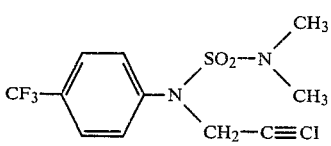

9. A compound according to claim 1, wherein such compound is N',N'-dimethyl-N-(3-iodopropargyl)-4-trifluoromethylthiosulphanilide of the formula

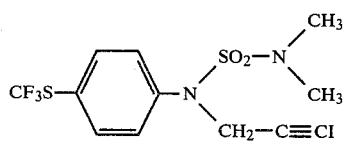

10. A compound according to claim 1, wherein such compound is N-methyl-N-(3-iodopropargyl)-4-morpholine sulphonamide of the formula

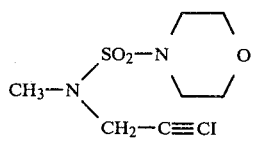

11. A compound according to claim 1, wherein such compound is N-(3-iodpropargyl)-N-phenyl-1-piperidine sulphonamide of the formula

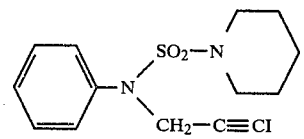

12. A compound according to claim 1, wherein such compound is piperidine amide of N-benzyl-N-(3-iodopropargyl)-1-piperidine sulphonamide of the formula

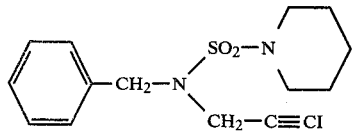

13. A microbicidal composition comprising a microbicidally effective amount of a compound according to claim 1 in admixture with a diluent.

14. The method of combatting microbes which comprises applying to such microbes or a microbe habitat a microbicidally effective amount of a compound according to claim 1.

15. The method according to claim 14, wherein such compound is

N',N'-dimethyl-N-(3-iodopropargyl)-4-methylsulphanilide,

N',N'-dimethyl-N-(3-iodopropargyl)-4-trifluoromethoxysulphanilide,

N',N'-dimethyl-N-(3-iodopropargyl)-4-fluorosulphanilide,

N',N'-dimethyl-N-(3-iodopropargyl)-4-trifluoromethylsulphanilide,

N',N'-dimethyl-N-(3-iodopropargyl)-4-trifluoromethylthiosulphanilide,

N-methyl-N(3-iodpropargyl)-4-morpholine sulphonamide,

N-(3-iodpropargyl)-N-phenyl-1-piperidine sulphonamide,

N-benzyl-N-(3-iodpropargyl)-1-piperidine sulphonamide.

* * * * *